United States Patent [19]

Dellinger et al.

[11] 4,183,141
[45] Jan. 15, 1980

[54] METHOD AND APPARATUS FOR TREATING MALOCCLUSION

[76] Inventors: Eugene L. Dellinger, 1326 Old Lantern Tr., Fort Wayne, Ind. 46825; Robert J. Loubier, 5122 Chippewa Ct., Fort Wayne, Ind. 46804

[21] Appl. No.: 857,373

[22] Filed: Dec. 5, 1977

[51] Int. Cl.² ............................................. A61C 7/00
[52] U.S. Cl. ................................. 32/66; 32/14 C
[58] Field of Search ................................. 32/14, 66

[56] References Cited
U.S. PATENT DOCUMENTS

| | | | |
|---|---|---|---|
| 3,345,745 | 10/1967 | Muller | 32/14 A |
| 3,477,128 | 11/1969 | Andrews | 32/14 A |
| 3,660,900 | 5/1972 | Andrews | 32/14 |
| 3,738,005 | 6/1973 | Cohen | 32/14 A |
| 3,871,098 | 3/1975 | Dean | 32/66 |
| 3,949,478 | 4/1976 | Schinhammer | 32/14 A |
| 4,014,096 | 3/1977 | Dellinger | 32/14 A |

Primary Examiner—Robert Peshock
Attorney, Agent, or Firm—Gust, Irish, Jeffers & Rickert

[57] ABSTRACT

An orthodontic method for treating malocclusion comprising the steps of forming a model of the patient's teeth in the form of a dental arch with the replicas of the teeth in idealized locations, establishing on the labial and buccal surfaces of the replicas locations which conjointly define an idealized dental arch configuration, forming rigid caps of hardenable, plastic material over the crowns of the replicas, affixing to the cap for each replica a bracket orientation module in registry with said established location and utilizing the caps with the respective bracket orientation modules to locate brackets on the corresponding teeth in the patient's mouth in locations corresponding to said established locations.

Bracket orientation modules are provided which are usable to locate precisely brackets on the teeth at the outset of treatment and also to replace any lost or damaged brackets anytime during treatment.

8 Claims, 15 Drawing Figures

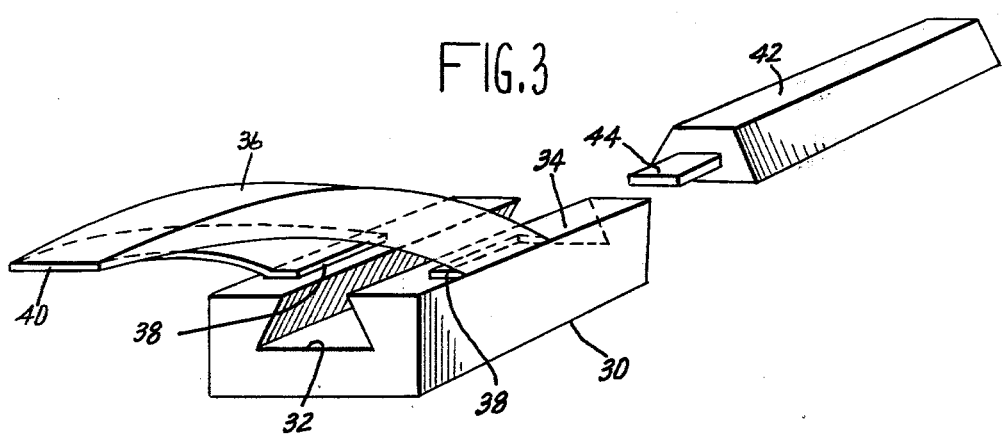
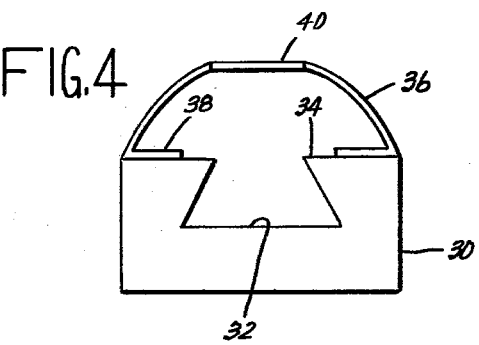
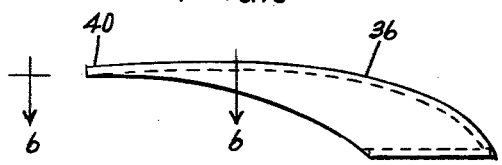
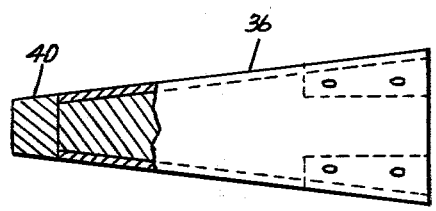
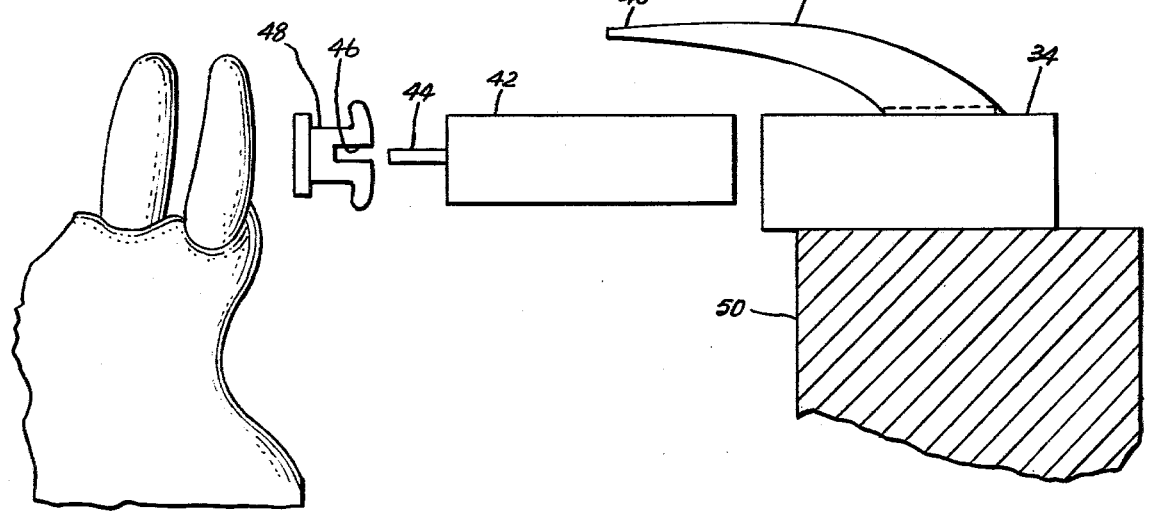

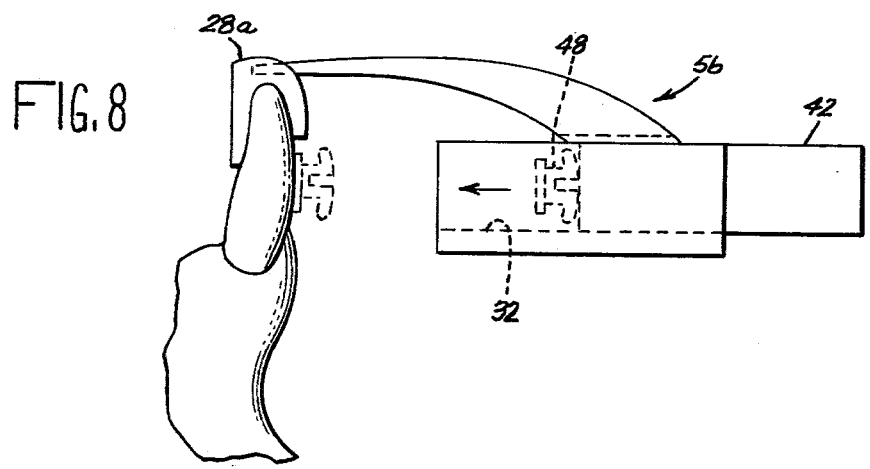
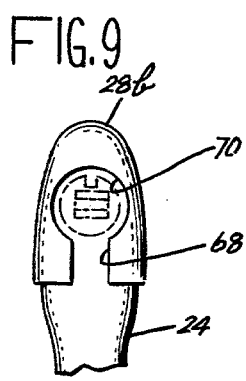
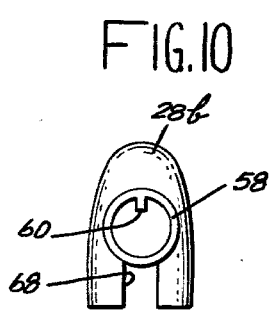
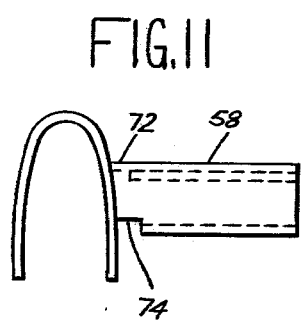
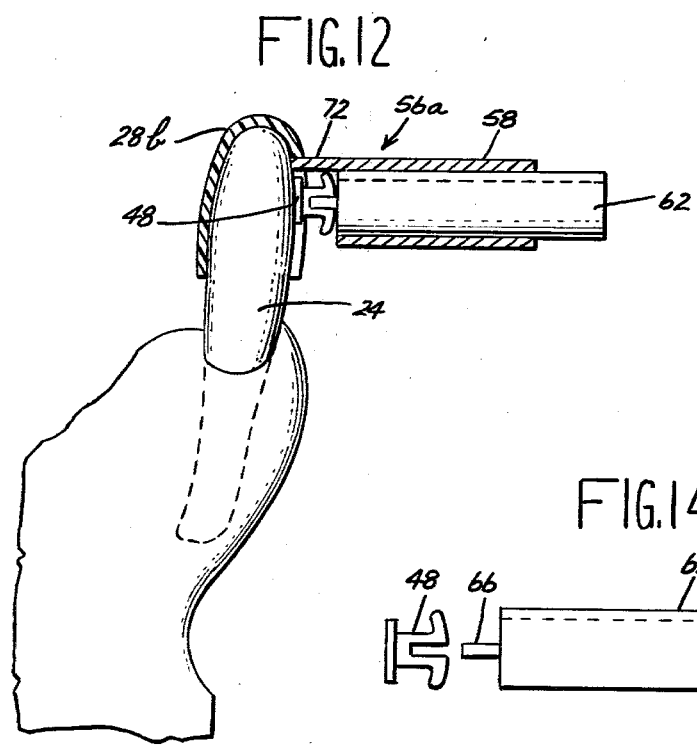
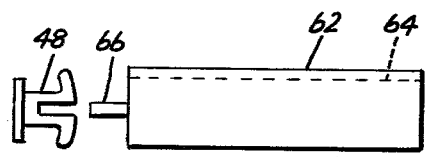
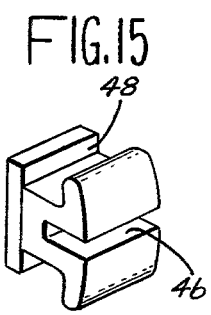

METHOD AND APPARATUS FOR TREATING MALOCCLUSION

BACKGROUND OF THE INVENTION

1. Field of the Invention

The present invention relates to orthodontics and more particularly to a method and apparatus for maintaining bracket position througout the period of treatment in accordance with a predetermined treatment plan.

2. Description of the Prior Art

Known prior art procedures are available to the orthodontist ideally to finish treatment with a coplanar arch wire having no buccal-lingual steps or other adjustment factors. Examples are disclosed in Dellinger U.S. Pat. No. 4,014,096 and Schinhammer U.S. Pat. No. 3,949,478. Of importance in following such procedures is the precise and correct placement of brackets upon the teeth, achieved by means of idealized laboratory models used to predetermine such placement. With reference to the Dellinger patent, band mounted brackets are finish fabricated on the model to conform to an idealized coplanar arch wire shape, while in the Schinhammer patent prefabricated brackets are ideally located on the model and eventually incorporated into a transfer mask conforming to the malocclusion for placement on the patient's teeth to initiate treatment. Further with respect to the Dellinger patent, an alternative is provided wherein a bracket-locating device is initially formed with reference to the estimated location of a bracket slot which is subsequently cut into a blank bracket mounted on the laboratory model. The bracket-locating device is then used to position the bracket on the tooth utilizing the post-formed slot. Should the estimated location be other than coincident with the post-formed slot, error in bracket placement results. Thus, the accuracy of placement depends upon the accuracy of the estimated slot location, an inexact technique at best.

In following the foregoing procedures with particular reference to direct bonding, it is intended to obtain the precise and correct placement of brackets on the teeth such that finished treatment with a coplanar arch wire may be achieved; however, during the relatively long period of treatment should there be a requirement to replace a bracket for some reason, such as a bracket having been lost or damaged, replacement in the same, precise, laboratory established position once again becomes an estimate and a matter of practitioner judgment and skill. Once bracket replacement is inaccurately performed, the original purpose of finish treatment with a coplanar arch wire, or an arch wire of desired configuration, can no longer be realized, thus diminuting the efficacy of the originally intended procedure.

Consequently, in order for the practitioner to obtain the desired end result, some method and apparatus are needed by means of which the precise and correct placement of brackets on the teeth can not only be achieved at the outset of treatment but also during treatment. Finish treatment could then be performed by means of a pre-configured arch wire, in the usual instance the preferred form being coplanar. By satisfying this need, the practitioner has complete control of the variables normally involved with the usual guesswork and corresponding judgment factors being eliminated. Also, this would result in reducing the degree of skill and time required on the part of the practitioner and in improved patient comfort during treatment.

SUMMARY OF THE INVENTION

The present invention relates to a technique in which the slots of the brackets on the patient's teeth upon completion of treatment are oriented to a pattern predetermined in a set of occluded models or master matrix units, the pattern being of coplanar, finite arch form. When treatment of the patient is completed, the bracket slots will define, for example, a coplanar continuum and the teeth will be aligned according to the idealized model. While a coplanar pattern is preferred in the usual instance, the pattern may include buccal-lingual steps as well as deviations from a common plane. However, when treatment is completed, the bracket slots will define a geometric pattern corresponding to the predetermined treatment pattern.

In the method of this invention, malocclusion is treated according to the steps of forming a model of the patient's teeth in the shape of a dental arch with the replicas of the teeth being disposed in idealized locations, establishing on the labial and buccal surfaces of the replicas locations which conjointly define an idealized dental arch configuration or arch wire shape, forming rigid caps of hardenable, plastic material over the crowns of the replicas in intimate conformity with the respective incisal edges, lingual, labial and buccal surfaces, securely affixing the guide portion of bracket orientation modules to the rigid caps, respectively, in registry with the aforesaid established locations, and finally utilizing the caps with the respective bracket orientation modules to locate the brackets on the corresponding teeth in the patient's mouth in the same locations as on the replicas. The caps with the attached bracket orientation modules are reusable throughout the period of treatment for the purpose of replacing a lost or damaged bracket in precisely the same position.

Apparatus for locating a bracket in a predetermined position on the labial or buccal surface of a tooth includes a rigid cap having an internal shape conforming to the crown portion of the tooth, and a guide element fixedly secured relative to said cap and having an elongated guiding portion which extends transversely to the axis of the tooth in registry with said predetermined position, the guiding portion having one end in registry with this predetermined position. A bracket-carrying member is slidably received for rectilinear movement by said guiding portion whereby said bracket-carrying member may be moved into registry with the predetermined position on the tooth. Means on one end of the bracket-carrying member carries a bracket and abuts the same against the tooth surface at said predetermined position.

It is an object of this invention to provide a method and apparatus which facilitates treatment of malocclusion.

It is another object of this invention to provide a method and apparatus which will enable a practitioner to maintain a predetermined plan of treatment throughout the period of treatment thereby to achieve a predetermined end result.

The above-mentioned and other features and objects of this invention and the manner of attaining them will become more apparent and the invention itself will be best understood by reference to the following description of an embodiment of the invention taken in conjunction with the accompanying drawings.

BRIEF DESCRIPTION OF THE DRAWINGS

FIG. 3 is an exploded view of one portion of the bracket-locating device of FIGS. 1 and 2;

FIG. 4 is an end view of the guide element of FIG. 3;

FIG. 5 is a side view of the frame portion attached to the guide element of FIG. 4;

FIG. 6 is a top view of the frame portion of FIG. 5 partially sectioned substantially along section line 6—6;

FIG. 7 is a fragmentary side view similar to that of FIG. 1 showing certain parts in exploded form for clarity;

FIG. 8 is a view similar to FIG. 7 showing the bracket-locating device in position for placing a bracket on the labial surface of a tooth;

FIG. 9 is a fragmentary elevation of the labial surface of a tooth with a portion of another embodiment of a bracket-locating device mounted thereon;

FIG. 10 is a view like that of FIG. 9 without the tooth but with a guide tube of the bracket-orienting module in place;

FIG. 11 is a side view of the device of FIG. 10;

FIG. 12 is an illustration, partly sectioned, of the device of the preceding FIGS. 9 through 11 being used to locate a bracket on the labial surface of a tooth;

FIG. 13 is an end view of the orienting tube of the device of FIGS. 9 through 12;

FIG. 14 is a side view of the bracket-carrying plunger which is slidably received by the tube of FIG. 13; and FIG. 15 is a perspective view of a typical bracket which may be direct bonded to the labial or buccal surface of a tooth.

DESCRIPTION OF THE ILLUSTRATED EMBODIMENTS

Figure 1:
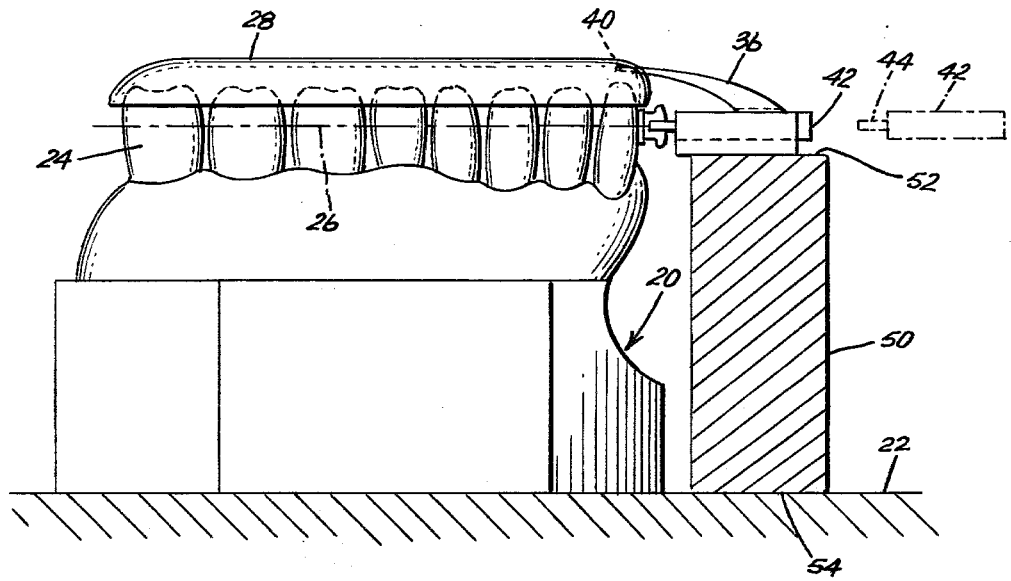
FIG. 1 is a side elevation, partly sectioned, of apparatus used in one step of the method of this invention.

In practicing the present invention, an idealized model of the patient's teeth is produced in the laboratory in accordance with the disclosure in Dellinger U.S. Pat. No. 4,014,096 which is incorporated herein by reference. Briefly, an impression of the patient's mouth is taken, and casting material is poured into the impression for the purpose of obtaining a working cast or model of the patient's teeth. The cast teeth or replicas are then sectioned from the working cast by any suitable method, such as cutting, and reset into a soft plastic media, such as wax, in an ideal or overtreated position as determined by the practitioner. The model thus created is in the form of an ideal occlusion or ideal overtreatment of the original malocclusion as determined by the practitioner, this model being the idealized model referred to hereinabove. Liquid acrylic, for example, is flowed around the stems of the sectioned replicas, which upon hardening, provides a rigid model of the idealized dental arch which may be handled as an integrated unit, referred to in the aforesaid U.S. Pat. No. 4,014,096 as the master matrix unit. Such a master matrix unit is indicated by the numeral 20 in FIGS. 1 and 2. The unit or model 20 is provided with a flat bottom surface which is rested on a flat horizontal surface 22 which serves as a reference from which height measurements are taken.

A coplanar line or mark 26 lying in a plane parallel to surface 22 is next drawn on the tooth replicas 24. The position of this line 26 on each replica 24 is selected by the clinician to coincide with the desired location of the slot in a bracket of the direct bond type. Thus, the line 26 around the entire dental arch will correspond to the shape of an arch wire, preferably smoothly curvilinear and coplanar, to be used in the final stages of treatment. Such an arch wire is disclosed in the aforesaid U.S. Pat. No. 4,014,096. Other line patterns determined by the arch wire shaped desired, can also be used.

A plastic cap 28 having the shape of the dental arch is formed over the crowns of the replicas 24 intimately to conform to the incisal edges and labial, buccal and lingual surfaces of the replicas 24, the material of the cap 28 preferably being plastic in liquid, semiliquid or moldable form which may be molded over the replica crown to the form shown and then permitted to harden. Also, the same material and techniques used in making the original impression from the patient's mouth may also be used. Preferably, such plastic material should be polymerizable such that once it has hardened, the heat of a patient's mouth will not soften or deform the same.

At some point in the formation of the cap 28 or in any event prior to the further processing thereof, a desired number of bracket-locating devices are secured thereto, typical of such devices being more clearly shown in FIGS. 1 through 7 for one embodiment and FIGS. 9 through 14 for a second embodiment. Referring to the first embodiment, the bracket-locating device is shown disassembled in FIG. 3. This device includes a guide block 30 of essentially rectangular shape having an elongated slot 32 of uniform keystone cross-section extending length-wise thereof. A curved but rigid arm 36 which may be fabricated of metal or plastic is suitably secured to the upper surface 34 of the block 30 in straddling relation to the open side of the slot 32 thereby to extend generally parallel to and above the longitudinal extent of the block 30 but therebeyond to an extent as shown more clearly in FIGS. 1 and 7. The arm 36 is illustrated as being fabricated of metal with inturned flanges 38 at the base secured to the upper surface 34 of the block 30 by means of threaded fasteners or a suitable polymerizable adhesive as desired. The arm 36 is generally tapered with the distal end 40 being essentially flat and extending generally parallel to the slot 32.

A plunger or bracket-carrying member 42 is elongated and shaped slidably to fit with minimal clearance the slot 32. On the end of the plunger 42 and in parallelism with the axis thereof is a bracket-carrying projection 44 sized slidably to fit, again with minimal clearance, the slot 46 (FIG. 7) normally provided in a bracket 48 of the direct bonding type.

Figure 2:
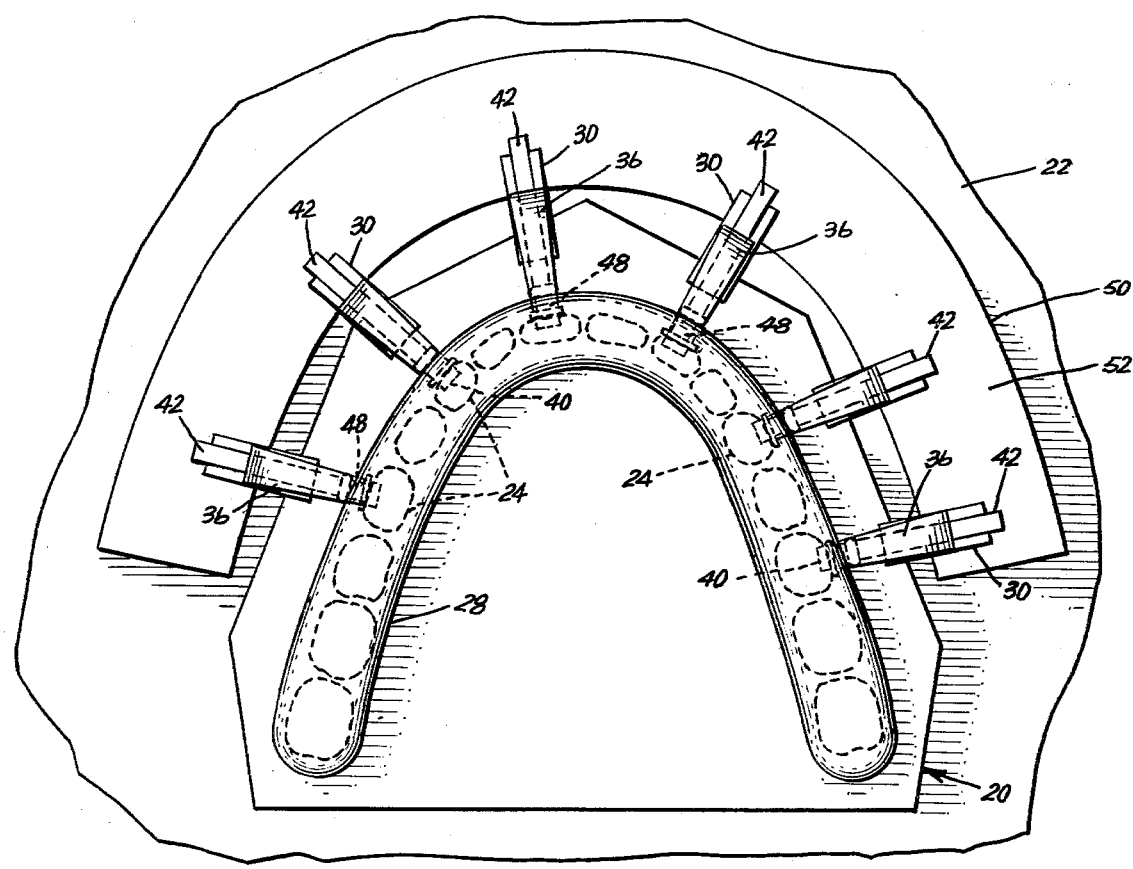
FIG. 2 is a top plan view thereof.

Referring now to FIGS. 1, 2 and 7, the bracket-locating device described thus far is fixedly secured to the cap 28, there being one device for each replica or tooth on which the practitioner intends to direct bond a bracket. As shown in FIG. 2, and for illustrative purposes only, six such modules are shown.

A U-shaped height gauge 50 having precisely parallel upper and lower surfaces 52 and 54 is positioned as shown on the reference table surface 22 symmetrically spaced relation from the arch of the model 20. The height gauge 50 has its upper surface 52 located such that with the plunger 42 received in the guide block 30 and the guide block 30 with its flat surface resting on the surface 52 as shown more clearly in FIGS. 1 and 7, the bracket-supporting projection 44 on the plunger 42 precisely registers with the line 26 marked on the respective replica 24. The point of contact between the tip of the projection 44 and the labial or buccal surface of the respective replica 24 may thus be characterized as the "established location", meaning that this is the corresponding location on the labial or buccal surface of the patient's tooth where the bracket will be bonded, the placement being such that the slot in the bracket will be in registry with an imaginary line on the patient's tooth which relates precisely with that on the corresponding replica.

With the bracket-locating device 30, 36, 42 so positioned as shown in FIG. 1, the distal end portion 40 of the supporting arm 36 is disposed to be secured within the body of the cap 28 or alternatively may be superposed thereon where it is secured in place by means of a suitable adhesive or threaded fastener. The devices 30, 36, 42 may be positioned before the cap 28 is molded such that upon formation thereof, the distal end portions 40 will be encapsulated within and thereby rigidly secured in place relative to the cap 28. As shown more clearly in FIG. 2, the devices and in particular the supporting arm 36 are oriented substantially perpendicular to the labial or buccal surface of the respective replica or tooth. Further, the slot 32 in the guide block 30 is oriented with its axis substantially normal to the labial or buccal surface of the replica. Thus, movement of the plunger 42 within the slot 32 results in movement of the bracket-carrying projection 44 along a line essentially normal to the axis of the respective tooth and in registry with the line 26. Further, the projection 44 is so positioned that with a bracket 48 mounted thereon, the latter can be positioned mesiodistally on the respective replica with the slot thereof in registry with line 26. This location of the bracket on the replica surface is referred to in the claims as the "established location".

Of importance is the fact that the bracket-locating devices 30, 36, 42 are rigidly secured to the cap 28 such that there is no relative movement or flexure therebetween. Thus, the material of the cap 28 as well as those for the bracket-locating device must be such as to prevent any such movement or flexure.

Upon completion of the cap 28 with the attached bracket-locating devices, the cap 28 is sectioned transversely to provide one cap for each replica as shown more clearly in FIG. 8, this cap being indicated by the numeral 28a. The cap 28a may have the lateral sides removed such that it will consist of labial, incisal and lingual portions only or in the alternative may entirely surround the crown of the replica. As the sectioned caps are removed from the respective replicas, they are identified in relation to the corresponding tooth for later use by the practitioner. The combination of the bracket-locating device and cap 28a of FIG. 8 is referred to hereinafter as the bracket orientation module generally indicated by the reference numeral 56.

In direct bonding brackets now to the patient's teeth, the practitioner utilizes the modules 56. With respect to a particular tooth, the practitioner selects the module 56 so identified. The cap 28a is placed over the crown of that tooth. Since that cap 28a has, in effect, been customized to fit intimately only that tooth, once it is fitted over the crown, the orientation module 56 becomes precisely registered with the location on the labial surface where the bracket is to be bonded.

Location and bonding of the bracket is accomplished by applying cement to the bracket foot or tooth in accordance with conventional practice, mounting the bracket 48 with the slot 46 thereof on the plunger projection 44, inserting the plunger 42 in the slot 32, sliding the latter toward the tooth to a point at which the bracket is firmly positioned on the tooth surface. The plunger 42 is held in this position until the cement cures or sets at which time the plunger 42 is retracted and the module 56 is removed from the tooth. Brackets are applied to the other teeth in the patient's mouth in the same manner. Once installed, an arch wire which may be of the smoothly curvilinear configuration already described is secured in the bracket slots in accordance with conventional practice. Assuming that none of the brackets become damaged or lost during the treatment period, once the teeth have been moved to positions at which the slots and the brackets are coplanar and otherwise conform to the shape of the coplanar arch wire, the treatment is essentially complete.

If during treatment the particular bracket becomes dislodged or is broken, it may be replaced by an identical bracket in precisely the same position by using the same module 56. Thus the replacement fits into the pattern of treatment the same as the original.

Another embodiment of a bracket orientation module is shown in FIGS. 9 through 12 and is indicated generally in FIG. 12 by the reference numeral 56a. In this embodiment, the caps 28b may be formed in the same manner as that of caps 28a or alternatively, on the idealized model, may be individually formed over the replicas 24. In this case the guide element is in the form of a tube 58a having a longitudinally extending key 60. A plunger 62 is slidably received by the tube 58 and is provided with a longitudinally extending slot 64 which receives with minimal clearance the key 60. Thus the plunger 62 may be reciprocated within the tube 58, being held against rotation by means of this key and slot connection. A projection 56 axially extends from the end of the plunger 62 and is shaped identically to the projection 44 on the previously described plunger 42.

The cap 28b extends over the tooth replica 24 to a position just short of the gingiva which gives it more bearing surface on the tooth or replica 24 than in the case of the cap 28a of FIG. 8, for example. The labial side of the cap 28b has a slot portion 68 (FIGS. 9 and 10) formed therein and further a circular opening 70 into which fits a part cylindrical portion 72 of the guide tube 58. The portion 72 of the guide tube is fixedly secured into the opening 70 by means of some suitable adhesive, the cutaway portion 74 of the tube 58 registering with the slot 68.

In using the module 56a to locate and install a bracket 48 onto a tooth, the device 56a with the plunger 62 removed therefrom is positioned on the tooth as shown in FIG. 12. The bracket 48 is mounted on the plunger projection 66 and the plunger 62 is inserted into the tube 58 and moved toward the labial or buccal surface of the tooth. Cement, as before, is applied prior to engaging the bracket foot thereagainst. Once the bracket 48 has been moved into position against the tooth surface, it is held in this position until the cement sets. The plunger is thereafter removed and the module 56a is lifted off the tooth, the cut-away portion or slot 68 and the undercut 74 in the tube 58 providing clearance with respect to the mounted bracket 48.

By utilizing the method and apparatus of this invention, brackets may be direct bonded to the teeth in a patient's mouth in precise and correct positions which will enable finishing treatment by means of a pre-configured arch wire which is coplanar without any buccal-lingual steps. However, the arch wire may be other than coplanar and provided with such steps as may be predetermined by the practitioner, the modules having been fabricated according to the predetermined arch wire shape. During treatment, should any bracket become dislodged or damaged, it can be replaced in precisely the same position as the original by utilizing the bracket orientation modules disclosed. Such modules are so constructed as to relate a bracket-guiding element in precise registry with the location on the tooth preestablished in the laboratory. This bracket-guiding element is then utilized to position precisely the bracket on the tooth surface.

Since all of the bracket-locating devices 56 and 56a are prefabricated in a laboratory in accordance with a predetermined plan of treatment (see FIGS. 1, 2 and 7, for example), much of the guesswork and many of the judgment factors involved conventionally in the selection and location of brackets on the part of the practitioner are eliminated, the locations of the brackets on the teeth being provided for the practitioner by means of the bracket orientation modules which relate to the arch wire shapes for final treatment.

While there have been described above the principles of this invention in connection with a specific method and apparatus, it is to be clearly understood that this description is made only by way of example and not as a limitation to the scope of the invention.

What is claimed is:

1. Apparatus for locating a bracket in a predetermined position on the labial or buccal surface of a tooth comprising a rigid cap having an internal shape conforming to the crown portion of a tooth, a hollow guide element fixedly secured relative to said cap and having an elongated guiding portion which extends transversely to and outwardly from the labial or buccal surface of the tooth with said guiding portion having one open end in registry with and spaced from the aforesaid predetermined position, the distance said open end is spaced from said predetermined position being greater than the height of a bracket to be mounted, a bracket-carrying member slidably received for rectilinear movement by said guiding portion whereby said member may be moved into registry with said predetermined position, and means on one end of said member for carrying a bracket and abutting the same against the tooth surface at said predetermined position.

2. The apparatus of claim 1 wherein the guiding portion of said guide element has elongated surfaces that form a slide of uniform cross-section, said bracket-carrying member being shaped in cross-section slidably to engage said slide, the engageable portions of said element and member including shapes that prevent relative rotation thereof.

3. The apparatus of claim 2 wherein a portion of the end of said guide element which is in registry with said predetermined position is contiguously rigidly secured to said cap.

4. The apparatus of claim 1 including a supporting arm secured at one end to said guide element and at the other end to said cap.

5. The apparatus of claim 4 wherein said guide element is an elongated block with said slide being a channel formed therein, said supporting arm being secured to one side of said block and to the crown portion of said cap, said bracket-carrying member being in the form of an elongated plunger having a shape which slidably fits said channel, said member having a tongue projecting from one end thereof adapted to engage the slot of a bracket.

6. The apparatus of claim 5 wherein said channel is of keystone cross-section and said predetermined position is the mesialdistal portion of said tooth.

7. The apparatus of claim 3 wherein said guide element is in the form of a tube secured at said one end in a companion opening in the side of said cap, said bracket-carrying member being an elongated plunger of a cross-section that slidably fits the interior of said tube, and a key and slot connection between said element and member for preventing relative rotation thereof, said plunger having a tongue projecting axially therefrom and adapted to fit the slot of a bracket.

8. In a method of orthodontics for treating malocclusion, the steps of:
 (a) forming a model of the patient's teeth in the shape of a dental arch with the replicas of the teeth in idealized locations,
 (b) establishing on the labial and buccal surfaces, respectively, of said replicas locations corresponding to bracket slots,
 (c) forming rigid caps of hardenable plastic material over at least a portion of the crowns of preselected replicas in intimate conformity with the respective incisal edges, lingual, labial and buccal surfaces, said forming step including forming a single arch shaped cap over all of the replicas of said model, and sectioning said arch shaped cap into multiple caps, one for each replica, respectively,
 (d) securely affixing the guide portion of bracket-locating devices to said rigid caps, respectively, in registry with said established locations, and
 (e) utilizing the caps with the respective guide portions to locate brackets on the corresponding teeth in the patient's mouth.

* * * * *